(12) United States Patent
Knapp et al.

(10) Patent No.: US 11,547,411 B2
(45) Date of Patent: Jan. 10, 2023

(54) ANASTOMOSIS WOUND PROTECTOR

(71) Applicant: Covidien LP, Mansfield, MA (US)

(72) Inventors: Robert H. Knapp, Middlebury, CT (US); Stanislaw Marczyk, Stratford, CT (US); Sachin Budhabhatti, Unionville, CT (US); Matthew Eschbach, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 73 days.

(21) Appl. No.: 16/752,884

(22) Filed: Jan. 27, 2020

(65) Prior Publication Data

US 2020/0268388 A1 Aug. 27, 2020

Related U.S. Application Data

(60) Provisional application No. 62/808,912, filed on Feb. 22, 2019.

(51) Int. Cl.
*A61B 17/115* (2006.01)
*A61B 17/11* (2006.01)

(52) U.S. Cl.
CPC ...... *A61B 17/1155* (2013.01); *A61B 17/1152* (2013.01); *A61B 17/1114* (2013.01); *A61B 2017/1135* (2013.01)

(58) Field of Classification Search
CPC ............ A61B 17/1155; A61B 17/1152; A61B 17/1114; A61B 2017/1135; A61B 2017/1132; A61B 2017/00951; A61B 17/07292; A61B 90/00; A61B 2017/1107; A61B 2017/00778

USPC .......................................... 227/175.1–182.1
See application file for complete search history.

(56) References Cited

U.S. PATENT DOCUMENTS

| 2,448,938 | A | | 9/1948 | Wayne | |
|---|---|---|---|---|---|
| 2,552,443 | A | * | 5/1951 | Molinari | A45C 3/045 224/601 |
| 2,753,829 | A | * | 7/1956 | Agra | E02B 3/26 114/219 |
| 3,193,165 | A | | 7/1965 | Akhalaya et al. | |
| 3,388,847 | A | | 6/1968 | Kasulin et al. | |
| 3,552,626 | A | | 1/1971 | Astafiev et al. | |
| 3,638,652 | A | | 2/1972 | Kelley | |
| 3,771,526 | A | | 11/1973 | Rudie | |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Jul. 24, 2020, issued in EP Appln. No. 20158697, 9 pages.

*Primary Examiner* — Robert F Long
(74) *Attorney, Agent, or Firm* — Carter, DeLuca & Farrell LLP

(57) ABSTRACT

A wound protector includes a tubular body that is configured to protect a cut site of an anastomosis. The wound protector can be secured to the anastomotic site after formation of the anastomosis or, alternatively, secured to the anastomotic site during formation of the anastomosis. The tubular body of the wound protector is positioned and configured to shield the anastomosis from waste material passing through a digestive tract of a patient.

17 Claims, 10 Drawing Sheets

(56) References Cited

U.S. PATENT DOCUMENTS

| | | | |
|---|---|---|---|
| 4,194,652 A * | 3/1980 | Williamson | B65D 88/1612 |
| | | | 112/475.08 |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,315,504 A * | 2/1982 | Drennan | A61F 13/102 |
| | | | 128/881 |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,583,577 A * | 4/1986 | Canfield | B65D 81/3879 |
| | | | 150/154 |
| 4,592,354 A | 6/1986 | Rothfuss | |
| 4,603,693 A | 8/1986 | Conta et al. | |
| 4,606,343 A | 8/1986 | Conta et al. | |
| 4,610,028 A * | 9/1986 | Nattrass | B65D 88/1681 |
| | | | 383/7 |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,674,664 A * | 6/1987 | Simon | A45F 3/04 |
| | | | 224/153 |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,083,555 A * | 1/1992 | Lewis | A45D 44/22 |
| | | | 450/69 |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,187,823 A * | 2/1993 | Ferguson | A45C 9/00 |
| | | | 190/1 |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,165 A * | 5/1995 | Ellis | A47B 88/90 |
| | | | 220/495.08 |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,456,062 A * | 10/1995 | Wechsler | B65D 33/28 |
| | | | 229/87.19 |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,503,638 A * | 4/1996 | Cooper | A61B 17/07207 |
| | | | 606/232 |
| 5,522,534 A | 6/1996 | Viola et al. | |
| 5,533,661 A | 7/1996 | Main et al. | |
| 5,588,579 A | 12/1996 | Schnut et al. | |
| 5,592,953 A * | 1/1997 | Delao | A61F 15/004 |
| | | | 128/882 |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,692,660 A * | 12/1997 | Stewart | A45C 3/00 |
| | | | 190/103 |
| 5,702,409 A * | 12/1997 | Rayburn | A61B 17/07207 |
| | | | 606/220 |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,743,458 A * | 4/1998 | French | B65D 23/08 |
| | | | 150/154 |
| 5,749,896 A | 5/1998 | Cook | |
| 5,758,814 A | 6/1998 | Gallagher et al. | |
| 5,765,748 A * | 6/1998 | Chen | B65D 5/68 |
| | | | 229/125.22 |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,845,994 A * | 12/1998 | Rice | A45C 1/04 |
| | | | 383/76 |
| 5,855,312 A | 1/1999 | Toledano | |
| 5,860,581 A | 1/1999 | Robertson et al. | |

(56) References Cited

U.S. PATENT DOCUMENTS

| | | | |
|---|---|---|---|
| 5,868,760 A | 2/1999 | McGuckin, Jr. | |
| 5,881,943 A | 3/1999 | Heck et al. | |
| 5,902,312 A * | 5/1999 | Frater | A61B 17/07207 |
| | | | 606/148 |
| 5,909,833 A * | 6/1999 | Smith | A45F 5/00 |
| | | | 224/577 |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,085,695 A * | 7/2000 | Miller | A01K 27/006 |
| | | | 119/795 |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,189,697 B1 * | 2/2001 | Davis | A45C 11/008 |
| | | | 206/373 |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,224,259 B1 * | 5/2001 | Guerra | D06F 95/006 |
| | | | 383/117 |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,286,798 B1 * | 9/2001 | Chun | A47G 23/0216 |
| | | | 206/218 |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,410 B1 * | 6/2002 | Guerra | D06F 95/006 |
| | | | 383/117 |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Dell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B1 | 6/2007 | McGuckin, Jr. | |
| 7,240,517 B2 * | 7/2007 | Barak | A44C 17/0283 |
| | | | 206/6.1 |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |

(56) References Cited

U.S. PATENT DOCUMENTS

| | | | |
|---|---|---|---|
| 7,455,682 B2 | 11/2008 | Viola | |
| 7,481,347 B2 | 1/2009 | Roy | |
| 7,494,038 B2 | 2/2009 | Milliman | |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,540,839 B2 | 6/2009 | Butler et al. | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,556,186 B2 | 7/2009 | Milliman | |
| 7,559,451 B2 | 7/2009 | Sharma et al. | |
| 7,585,306 B2 | 9/2009 | Abbott et al. | |
| 7,588,174 B2 | 9/2009 | Holsten et al. | |
| 7,600,663 B2 | 10/2009 | Green | |
| 7,611,038 B2 | 11/2009 | Racenet et al. | |
| 7,635,385 B2 | 12/2009 | Milliman et al. | |
| 7,661,223 B2 * | 2/2010 | Dudney | A01K 97/08 |
| | | | 43/26 |
| D612,744 S * | 3/2010 | Childs | D9/706 |
| 7,669,747 B2 | 3/2010 | Weisenburgh, II et al. | |
| 7,686,201 B2 | 3/2010 | Csiky | |
| 7,694,864 B2 | 4/2010 | Okada et al. | |
| 7,699,204 B2 | 4/2010 | Viola | |
| 7,708,181 B2 | 5/2010 | Cole et al. | |
| 7,717,313 B2 | 5/2010 | Criscuolo et al. | |
| 7,721,932 B2 | 5/2010 | Cole et al. | |
| 7,726,539 B2 | 6/2010 | Holsten et al. | |
| 7,743,958 B2 | 6/2010 | Orban, III | |
| 7,744,627 B2 | 6/2010 | Orban, III et al. | |
| 7,770,776 B2 | 8/2010 | Chen et al. | |
| 7,771,440 B2 | 8/2010 | Ortiz et al. | |
| 7,776,060 B2 | 8/2010 | Mooradian et al. | |
| 7,793,813 B2 | 9/2010 | Bettuchi | |
| 7,802,712 B2 | 9/2010 | Milliman et al. | |
| 7,823,592 B2 | 11/2010 | Bettuchi et al. | |
| 7,837,079 B2 | 11/2010 | Holsten et al. | |
| 7,837,080 B2 | 11/2010 | Schwemberger | |
| 7,837,081 B2 | 11/2010 | Holsten et al. | |
| 7,845,536 B2 | 12/2010 | Viola et al. | |
| 7,845,538 B2 | 12/2010 | Whitman | |
| 7,857,187 B2 | 12/2010 | Milliman | |
| 7,886,951 B2 | 2/2011 | Hessler | |
| 7,896,215 B2 | 3/2011 | Adams et al. | |
| 7,900,806 B2 | 3/2011 | Chen et al. | |
| 7,909,039 B2 | 3/2011 | Hur | |
| 7,909,219 B2 | 3/2011 | Cole et al. | |
| 7,909,222 B2 | 3/2011 | Cole et al. | |
| 7,909,223 B2 | 3/2011 | Cole et al. | |
| 7,913,892 B2 | 3/2011 | Cole et al. | |
| 7,918,377 B2 | 4/2011 | Measamer et al. | |
| 7,922,062 B2 | 4/2011 | Cole et al. | |
| 7,922,743 B2 | 4/2011 | Heinrich et al. | |
| 7,931,183 B2 | 4/2011 | Orban, III | |
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,025,685 B2 * | 9/2011 | Stewart | A61B 17/685 |
| | | | 606/302 |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,405 B2 | 2/2012 | Milliman | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,317,823 B2 * | 11/2012 | Pavcnik | A61F 6/24 |
| | | | 623/23.72 |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |

(56) References Cited

U.S. PATENT DOCUMENTS

| | | |
|---|---|---|
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,978,954 B2 * | 3/2015 | Shelton, IV ...... A61B 17/07207 227/175.1 |
| 9,010,608 B2 * | 4/2015 | Casasanta, Jr. .. A61B 17/07292 227/176.1 |
| 9,010,609 B2 * | 4/2015 | Carter ................ A61B 17/1155 227/176.1 |
| 9,022,274 B2 | 5/2015 | Penna |
| 9,433,416 B2 * | 9/2016 | Beardsley .............. A61B 17/32 |
| 9,655,620 B2 | 5/2017 | Prescott et al. |
| 11,197,672 B2 * | 12/2021 | Dunki-Jacobs ........ A61B 17/26 |
| 2002/0140183 A1 * | 10/2002 | Santiago-Diaz ......... F16J 3/041 277/634 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2005/0187576 A1 * | 8/2005 | Whitman ............. A61B 17/068 227/176.1 |
| 2006/0000869 A1 | 1/2006 | Fontayne |
| 2006/0011698 A1 | 1/2006 | Okada et al. |
| 2006/0100067 A1 * | 5/2006 | Washburn ............ A63B 69/201 482/83 |
| 2006/0201989 A1 | 9/2006 | Ojeda |
| 2006/0226038 A1 * | 10/2006 | Lampley ................... A45F 5/00 206/315.9 |
| 2006/0229643 A1 * | 10/2006 | Nolan .................. A61B 17/1114 606/153 |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0246505 A1 * | 10/2007 | Pace-Floridia .. A61B 17/07207 227/175.1 |
| 2008/0215087 A1 * | 9/2008 | Pavcnik ........... A61B 17/12113 128/831 |
| 2009/0043334 A1 | 2/2009 | Bauman et al. |
| 2009/0163934 A1 * | 6/2009 | Raschdorf, Jr. .. A61B 17/00234 606/139 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0306776 A1 * | 12/2009 | Murray .................... A61L 17/12 623/13.12 |
| 2009/0312775 A1 * | 12/2009 | Gilkey ................. A61B 17/068 606/147 |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0087279 A1 * | 4/2011 | Shah ................ A61B 17/07207 606/219 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0282446 A1 | 11/2011 | Schulte |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0234900 A1 * | 9/2012 | Swayze ............ A61B 17/07207 227/180.1 |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0038151 A1 * | 2/2014 | Hart ....................... G09B 23/28 434/262 |
| 2014/0131418 A1 * | 5/2014 | Kostrzewski .... A61B 17/07292 227/176.1 |
| 2014/0158741 A1 * | 6/2014 | Woodard, Jr. ...... A61B 17/0401 227/175.1 |
| 2015/0351764 A1 * | 12/2015 | Shelton, IV ........... A61B 17/08 227/176.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0192937 A1 * | 7/2016 | De Oliveira ........ A61B 17/1114 227/175.1 |
| 2016/0302792 A1 | 10/2016 | Motai |
| 2016/0302950 A1 * | 10/2016 | Marmur ..................... A61F 2/07 |
| 2018/0036000 A1 * | 2/2018 | Terada ............... A61B 17/0483 |
| 2018/0085124 A1 | 3/2018 | Nativ et al. |
| 2020/0022704 A1 * | 1/2020 | Barrasa Shaw .... A61B 17/0469 |
| 2021/0353294 A1 * | 11/2021 | Aravalli ............. A61B 17/07292 |

FOREIGN PATENT DOCUMENTS

| | | | |
|---|---|---|---|
| CA | 3041249 A1 * | 11/2019 | ........... A61B 17/072 |
| CA | 3041257 A1 * | 11/2019 | ....... A61B 17/07207 |
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |

(56) References Cited

FOREIGN PATENT DOCUMENTS

| | | | |
|---|---|---|---|
| EP | 0503689 | A2 | 9/1992 |
| EP | 1354560 | A2 | 10/2003 |
| EP | 2138118 | A2 | 12/2009 |
| EP | 2168510 | A1 | 3/2010 |
| EP | 2238926 | A2 | 10/2010 |
| EP | 2524656 | A2 | 11/2012 |
| FR | 1136020 | A | 5/1957 |
| FR | 1461464 | A | 2/1966 |
| FR | 1588250 | A | 4/1970 |
| FR | 2443239 | A1 | 7/1980 |
| GB | 1185292 | A | 3/1970 |
| GB | 2016991 | A | 9/1979 |
| GB | 2070499 | A | 9/1981 |
| JP | 2004147969 | A | 5/2004 |
| JP | 2013138860 | A | 7/2013 |
| NL | 7711347 | A | 4/1979 |
| SU | 1509052 | A1 | 9/1989 |
| WO | 8706448 | A1 | 11/1987 |
| WO | 8900406 | A1 | 1/1989 |
| WO | 9006085 | A1 | 6/1990 |
| WO | 98/35614 | A1 | 8/1998 |
| WO | 0154594 | A1 | 8/2001 |
| WO | 2008107918 | A1 | 9/2008 |

\* cited by examiner

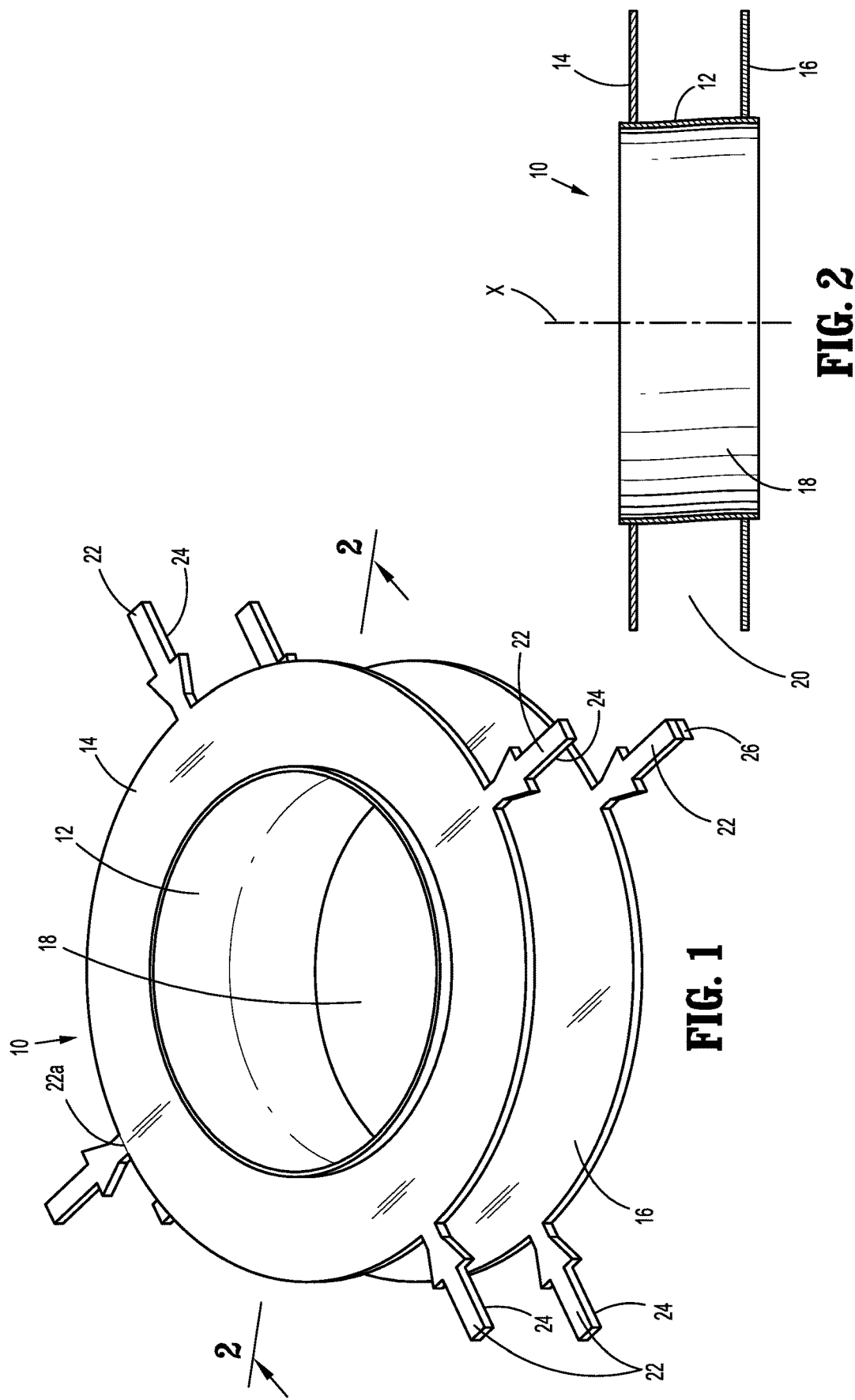

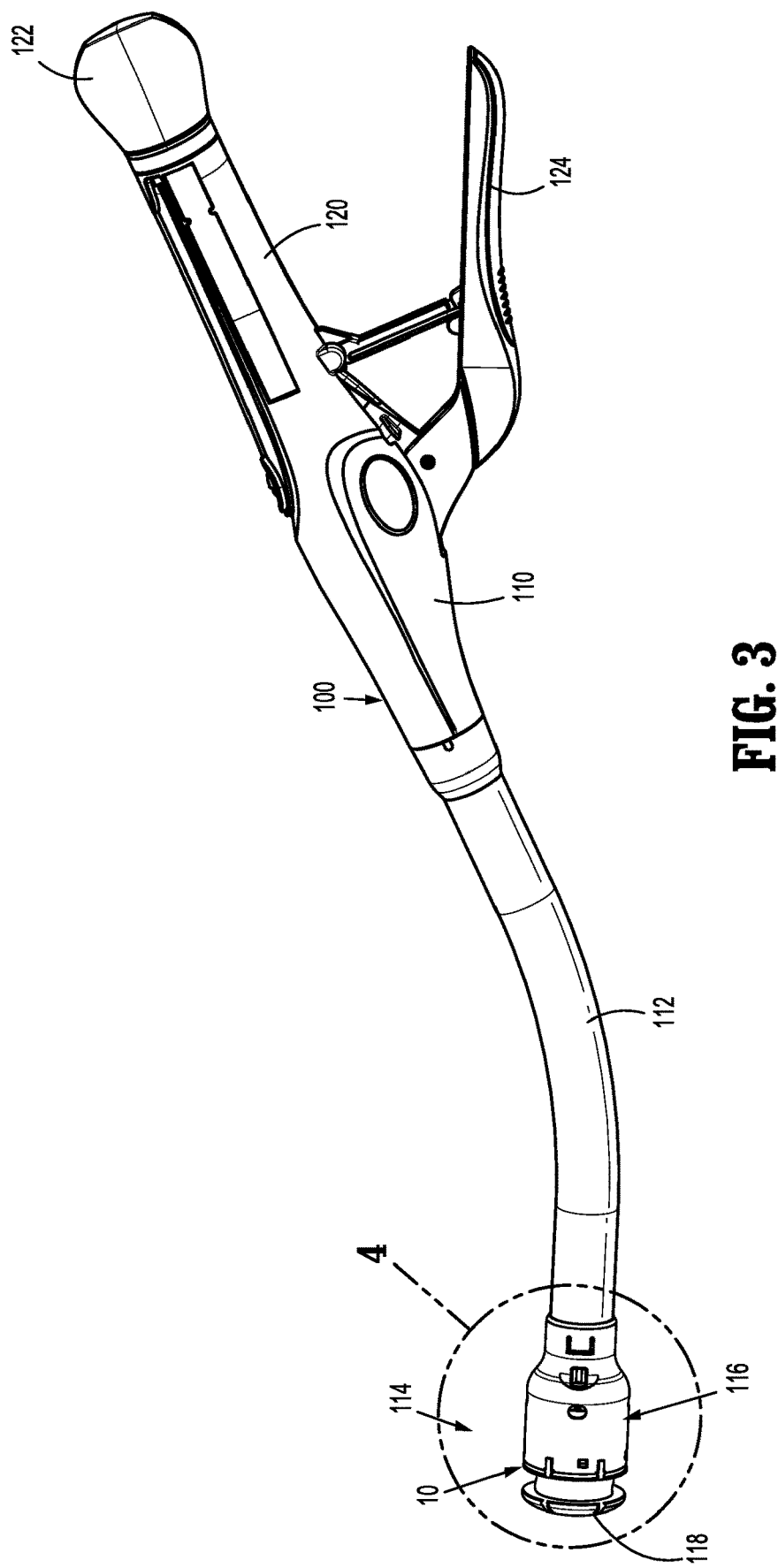

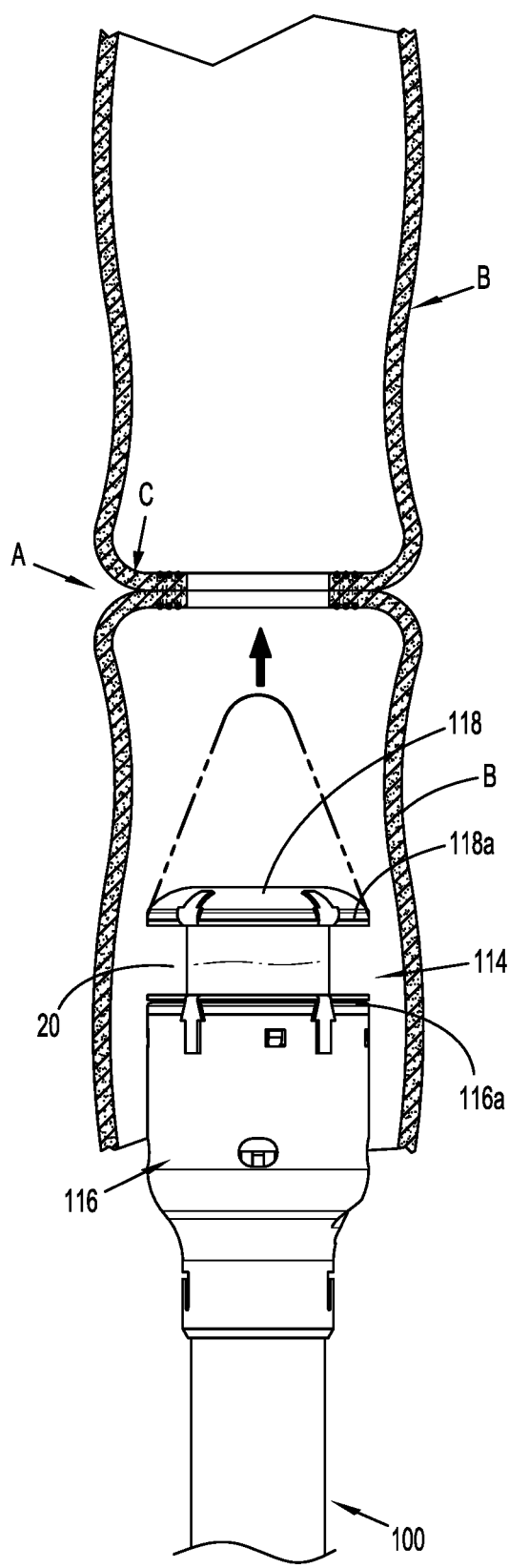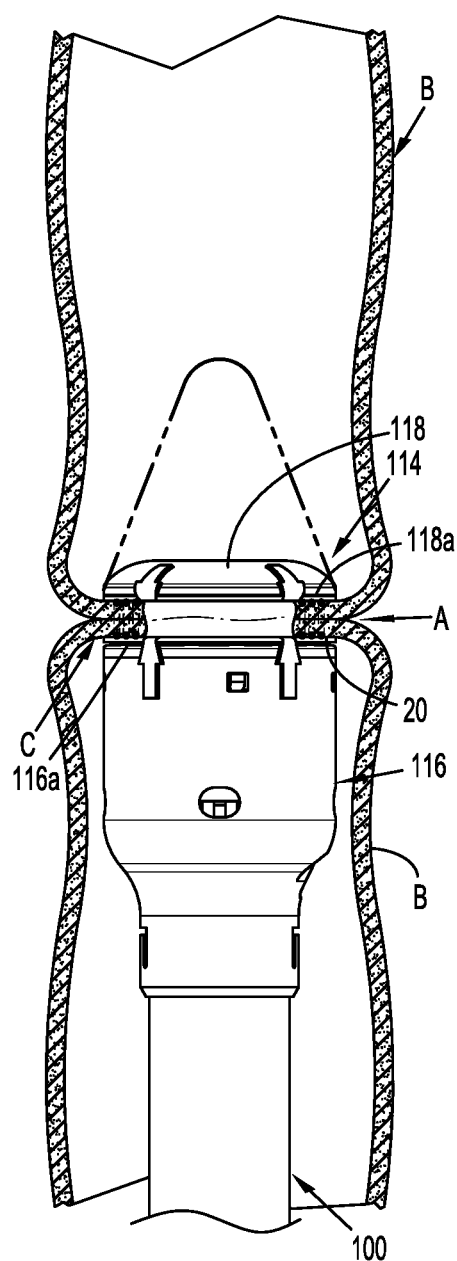
FIG. 5
FIG. 6

ANASTOMOSIS WOUND PROTECTOR

CROSS-REFERENCE TO RELATED APPLICATIONS

This application claims the benefit of and priority to U.S. Provisional Patent Application Ser. No. 62/808,912 filed Feb. 22, 2019, the entire disclosure of which is incorporated by reference herein

BACKGROUND

1. Technical Description

The present disclosure is directed to wound protectors and, more particularly, to wound protectors configured for placement during or after anastomosis procedures to protect a cut site of the anastomosis.

2. Background of Related Art

Anastomotic surgery is used to connect ends of two hollow lumen sections together. When the hollow lumen sections are both tubular, the anastomotic surgical technique used to connect the lumen sections is referred to as end-to-end anastomosis. An end-to-end anastomosis procedure leaves a ring-shaped flap of tissue within the connected hollow lumen sections having a cut-site on an inner most section of the flap.

End-to-end anastomosis procedures can be performed using stapling or suturing techniques. Although stapling techniques have been determined to result in a reduced occurrence of leakage, leakage still using both stapling and suturing techniques. Leakage at the cut site of an anastomosis may result in higher morbidity rates, patient suffering, increased cost, and even mortality.

There are multiple causes of leakage at the cut site of an anastomosis including necrosis of tissue and loosening of staple or suture lines. Harmful substances such as acids or unwanted bacteria may affect the healing process when exposed to the cut tissue. In addition, forces exerted on the cut site of the anastomosis as substances pass through the connected hollow lumen sections may also adversely impact the anastomosis.

Accordingly, a continuing need exists in the surgical arts for an improved device and procedure for protecting the cut site of an anastomosis either during or after an anastomosis procedure is performed.

SUMMARY

One aspect of the present disclosure is directed to a method of protecting a cut site of an anastomosis that includes positioning a tool assembly of a circular stapling device including a wound protector with a first flange supported on an anvil of the tool assembly and a second flange supported on a staple cartridge of the tool assembly within a body lumen defined by first and second body lumen sections; positioning ends of first and second body lumen sections within a pocket defined between the first and second flanges and a body portion of the wound protector; approximating the tool assembly to compress the ends of the first and second body lumen sections between the anvil and the staple cartridge; and firing the circular stapling device to staple the first and second flanges to the ends of the first and second body lumen sections to secure the cut site of the anastomosis within the pocket of the wound protector.

In embodiments, a circular stapling device is used to form the anastomosis prior to positioning the first and second body lumen sections within the pocket.

In some embodiments, the method further includes securing the wound protector onto the circular stapling device.

In certain embodiments, securing the wound protector onto the circular stapling device includes attaching a first fastening strip formed on the first flange of the wound protector to the anvil and attaching a second fastening strip formed on the second flange to a shell assembly of the tool assembly supporting the staple cartridge.

In embodiments, securing the wound protector onto the circular stapling device includes attaching a plurality of first fastening strips formed on the first flange to the anvil and attaching a plurality of second fastening strips formed on the second flange to a shell assembly of the tool assembly supporting the staple cartridge.

In some embodiments, securing the wound protector onto the circular stapling device includes removing cover strips from the first and second fastening strips.

Another aspect of the present disclosure is directed to a method of forming and protecting an anastomosis that includes positioning a tool assembly of a circular stapling device including an anvil and wound protector assembly into a body lumen of a patient formed from first and second body lumen sections; positioning ends of the first and second body lumen sections about a center rod of the anvil and wound protector assembly such that the ends of the first and second body lumen sections are positioned between an anvil surface of an anvil assembly of the anvil and wound protector assembly and a staple cartridge of the tool assembly; approximating the anvil assembly and the staple cartridge to clamp the ends of the first and second body lumen sections between a first end portion of a wound protector of the anvil and wound protector assembly that is secured to the anvil surface and the staple cartridge; firing the circular stapling device to secure the first end portion of the wound protector to the ends of the first and second lumen sections to form the anastomosis; and withdrawing the anvil assembly through the anastomosis to pull a second end portion of the would protector secured to a distal face of an anvil head of the anvil assembly through the anastomosis to invert the wound protector and provide a protective covering for the anastomosis.

In embodiments, withdrawing the anvil assembly through the anastomosis further includes manipulating the anvil assembly to disengage a tether having a first end secured to the second end portion of the wound protector and a second end secured to the anvil head from the anvil head.

Yet another aspect of the present disclosure is directed to a wound protector including an annular body, at least one firing strip, and a removable cover strip. The annular body of the wound protector has a first end portion and a second end portion, a first flange extending radially outwardly from the first end portion, and a second flange extending radially outwardly from the second end portion. The at least one fastening strip extends from each of the first and second flanges and includes a first side having an adhesive. The removable cover strip covers the adhesive on each of the fastening strips.

In embodiments, the at least one fastening strip includes a plurality of fastening strips positioned about the first and second flanges.

In some embodiments, the at least one fastening strip includes a tear line to facilitate separation of the at least one fastening strip from the first and second flanges.

Yet another aspect of the present disclosure is directed to an anvil and wound protector assembly including an anvil assembly, a wound protector, and at least one tether. The anvil assembly includes a center rod and an anvil head. The center rod has a distal portion and a proximal portion. The anvil head is supported on the distal portion of the center rod and includes a distal face and a proximally facing anvil surface. The wound protector has a tubular body having a first end portion that is secured to the proximally facing anvil surface and a second end portion positioned distally of the distal face of the anvil head such that the anvil head is supported within the tubular body of the wound protector. The at least one tether has a first end secured to the second end portion of the tubular body of the wound protector at a position distally of the distal face of the anvil assembly and a second end attached to the distal face of the anvil head.

In embodiments, the first open end portion of the tubular body of the wound protector is secured to the proximally facing surface with using an adhesive.

In some embodiments, the second end of the at least one tether is secured to the distal face of the anvil head using an adhesive.

In certain embodiments, the second end of the at least one tether is tied to the distal face of the anvil head.

In embodiments, the anvil head includes a hook and the second end of the at least one tether includes a loop that is secured to the hook.

In some embodiments, the at least one tether includes two tethers.

BRIEF DESCRIPTION OF THE DRAWINGS

Various embodiments of the presently disclosed wound protector are described herein below with reference to the drawings, wherein:

FIG. 1 is a side perspective view of an exemplary embodiment of the presently disclosed anastomotic wound protector;

FIG. 2 is a cross-sectional view taken along section line 2-2 of FIG. 1;

FIG. 3 is a side perspective view of the wound protector shown in FIG. 1 supported on a circular stapling device;

FIG. 5 is a side partial cross-sectional view of the wound protector and circular stapling device shown in FIG. 4 positioned within a body vessel adjacent an anastomosis prior to approximation and firing of the circular stapling device;

FIG. 6 is a side partial cross-sectional view of the wound protector and circular stapling device shown in FIG. 4 positioned within the body vessel about the anastomosis after approximation and firing of the circular stapling device;

DETAILED DESCRIPTION OF EMBODIMENTS

Figure 4:
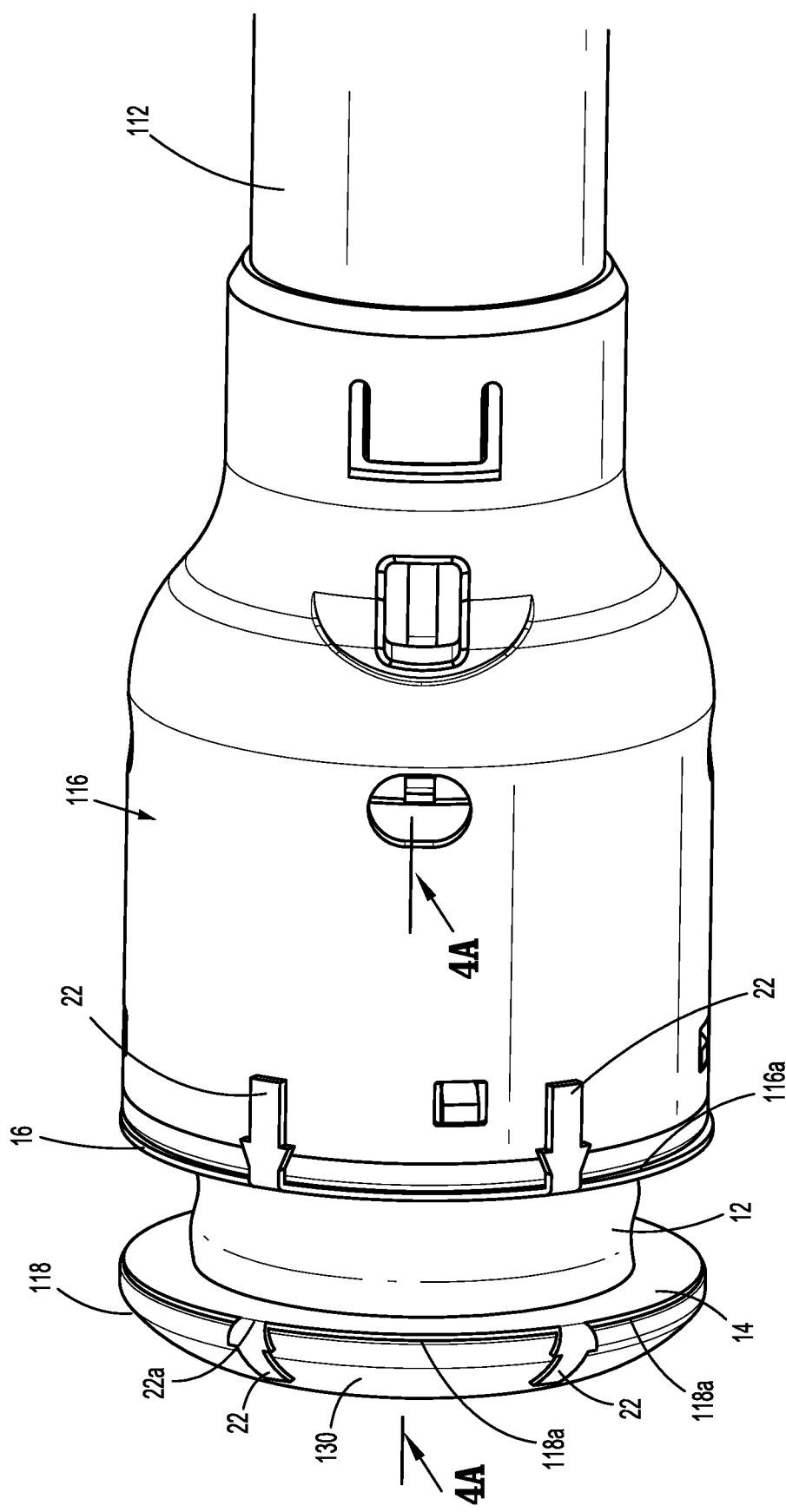
FIG. 4 is an enlarged view of the indicated area of detail shown in FIG. 3.

Exemplary embodiments of the presently disclosed wound protector will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Referring to FIGS. 1 and 2, the presently disclosed wound protector is shown generally as wound protector 10 and includes an annular body 12 defining a longitudinal axis "X" (FIG. 2), a first flange 14 that is attached to one end portion of the annular body 12, and a second flange 16 that is attached to the other end portion of the annular body 12. The annular body 12 defines a through bore 18 that extends along the longitudinal axis "X" through the wound protector 10. The first flange 14 and the second flange 16 are spaced from each other along the longitudinal axis "X" of the annular body 12 and extend in a direction radially outwardly of the longitudinal axis "X" to define a pocket or recess 20. In embodiments, the pocket 20 is configured and dimensioned to receive the cut site "C" of an anastomosis "A" (FIG. 5) or other wound that may require protection (FIG. 5). In some embodiments, the pocket 20 is annular to receive the entire cut site "C" of a circular anastomosis, e.g., anastomosis "A".

In embodiments, each of the first and second flanges 14, 16 includes fastening strips 22 that facilitate attachment of the wound protector 10 to a tool assembly 114 (FIG. 3) of a circular stapling device 100 as described in detail below. Each of the fastening strips 22 may have an adhesive 24 positioned on one side of the fastening strip 22 to facilitate securement of the fastening strips 22 to the tool assembly 114. In embodiments, the adhesive 24 of the fastening strips 22 can be enclosed by cover strips 26 that can be removed prior to attachment of the fastening strips 22 to the tool assembly 114. The fastening strips 22 may include perforations or a tear line 22a (FIG. 1) to allow for separation of the fastening strips 22 from the flanges 14, 16 after the anastomosis has been performed.

Figure 4A:
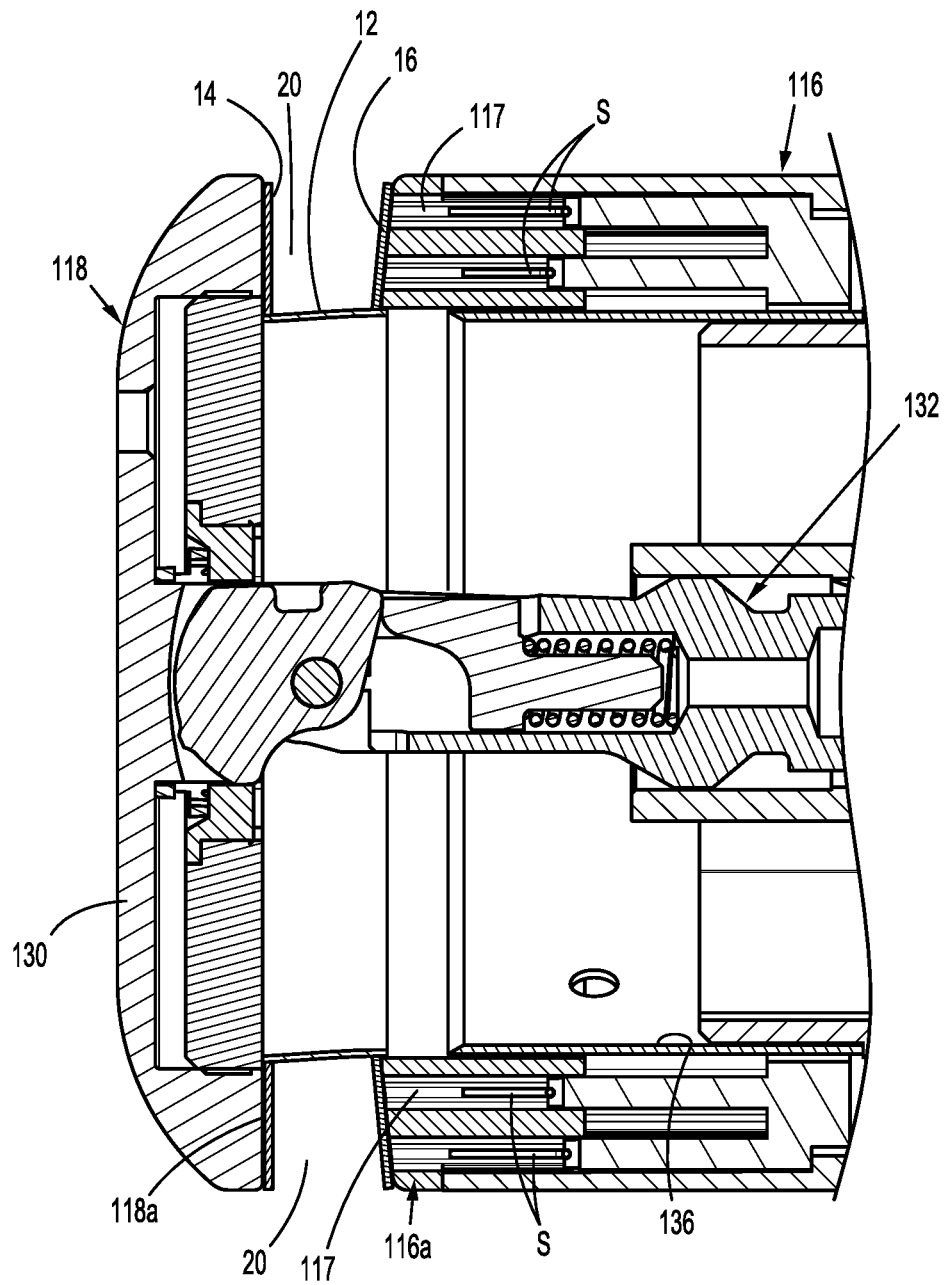
FIG. 4A is a cross-sectional view taken along section line 4A-4A of FIG. 4.

Referring also to FIGS. 3-4A, in embodiments, the wound protector 10 can be positioned about the cut site "C" (FIG. 5) of the anastomosis "A" by the circular stapling device 100. In embodiments, the circular stapling device 100 includes a handle assembly 110 (FIG. 3), an elongate body or adaptor 112, and a tool assembly 114. The tool assembly 114 includes a shell assembly 116 and an anvil assembly 118. The shell assembly 116 supports a staple cartridge 116a that includes a plurality of staple pockets 117 (FIG. 4A) that receive staples "S" (FIG. 4A). The anvil assembly 118 includes an anvil 118a that defines staple deforming pockets (not shown) that are positioned to receive the staples "S" from the staple pockets 117 to deform legs of the staples "S" as is known in the art.

The handle assembly 110 includes a stationary handle portion 120, an approximation knob 122 and a firing trigger 124. The approximation knob 122 is rotatable in relation to the stationary handle portion 120 to actuate an approximation assembly (not shown) of the circular stapling device 100 and move the anvil 118a of the anvil assembly 118 in relation to the staple cartridge 116a of the shell assembly 116 between a first position spaced from the staple cartridge 116a (FIG. 5) and an approximated position (FIG. 6) in juxtaposed alignment with the staple cartridge 116a. When the circular stapling device 100 is in the approximated position, the firing trigger 124 is movable towards the stationary handle portion 120 to fire staples "S" from the staple cartridge 116a of the shell assembly 116 into the staple deforming pockets of the anvil 118a.

The anvil assembly 118 includes an anvil head 130 that supports the anvil 118a and a center rod 132 (FIG. 4A). The circular stapling device 100 includes an anvil retainer (not shown) that is positioned within and extends from a distal end of the shell assembly 116 when the circular stapling device 100 is in a fully unapproximated position. The center rod 132 is configured to be releasably coupled to the anvil retainer to secure the anvil assembly 118 to the circular stapling device 100. For a more detailed description of various components of known circular stapling devices, see U.S. Pat. Nos. 7,303,106, 7,942,302, 9,022,274 and 9,655,620 which are incorporated herein by reference in their entirety.

Referring to FIG. 4A, in use, the wound protector 10 is positioned about the center rod 132 of the anvil assembly 118 and the center rod 132 is coupled to the anvil retainer (not shown). After the anvil assembly 118 is coupled to the anvil retainer, the first flange 14 of the wound protector 10 is secured to the anvil 118a of the anvil head 130 using the fastening strips 22 (FIG. 4) to cover the staple deforming pockets (not shown) of the anvil 11a. Similarly, the second flange 16 is secured to the shell assembly 116 using the fastening strips 22 to cover the staple pockets 117. As discussed above, the fastening strips 22 can have an adhesive 24 on one side of the fastening strip 22 to facilitate securement of the wound protector 10 to the shell assembly 116 and anvil assembly 118. When the wound protector 10 is attached to the tool assembly 114 of the stapling device 100, the first flange 14 is positioned on the anvil 118a of the anvil head 130 and the second flange 116a is positioned on a distal face of the staple cartridge 116a.

In embodiments, the circular stapling device 100 may be provided with the wound protector 10 already installed on the tool assembly 114. It is also envisioned that the circular stapling device 100 need not be provided with a knife 136 (FIG. 4A) because the wound protector 10 can be secured to the anastomosis "A" after the anastomosis procedure has been completed.

Figure 7:
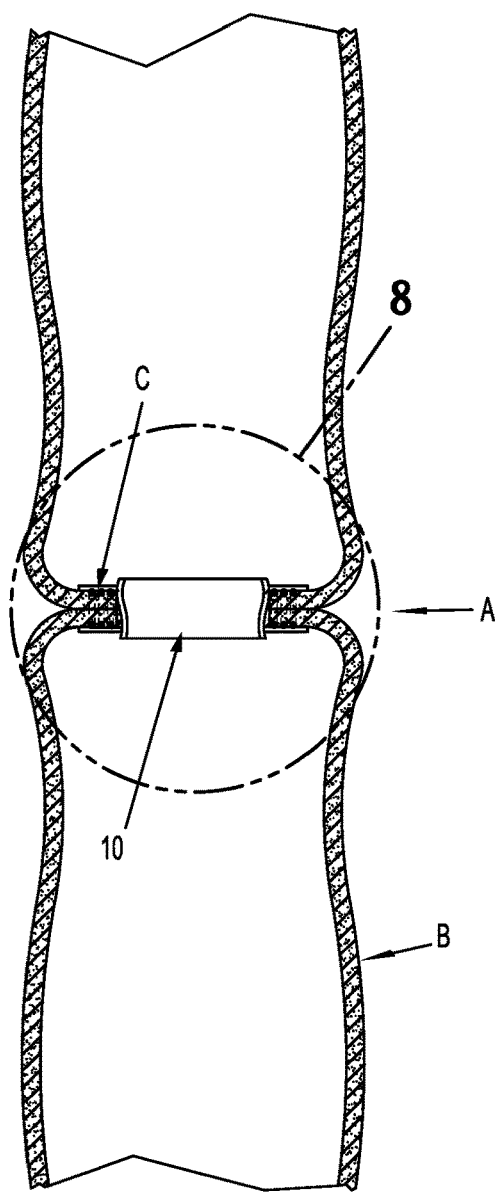
FIG. 7 is a side view of the wound protector shown in FIG. 1 positioned within the body vessel about the anastomosis after the circular stapling device has been removed from the body vessel.
Figure 8:
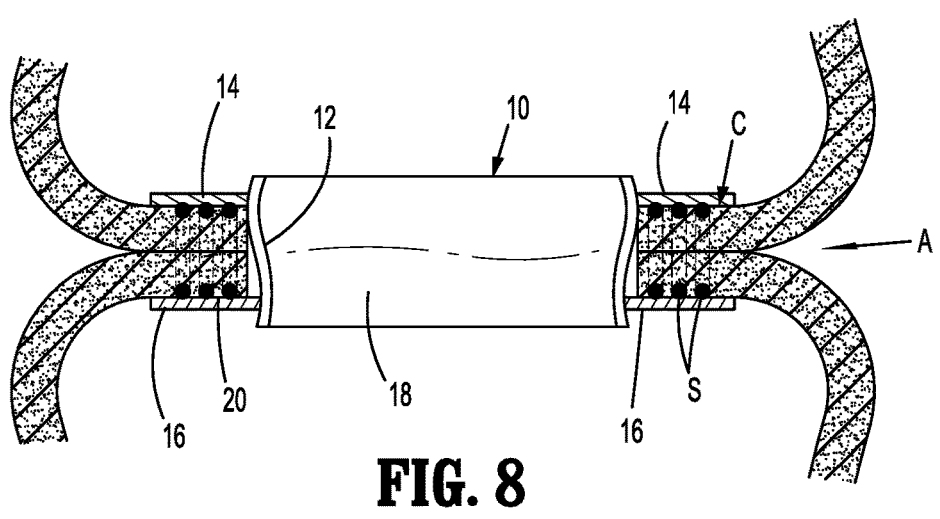
FIG. 8 is an enlarged view of the indicated area of detail shown in FIG. 7.

Referring to FIGS. 5-8, in order to attach the wound protector 10 to an anastomosis "A" to protect the cut site "C", the tool assembly 114 of the circular stapling device 100 is positioned within a body lumen "B" and advanced to a position adjacent cut site "C" of the anastomosis "A". Next, the circular stapling device 100 is manipulated to position the cut site "C" of the anastomosis "A" within the pocket 20 defined by the first and second flanges 14, 16, and the annular body 12 of the wound protector 10. After the cut site "C" is properly positioned within the pocket 20 of the wound protector 10, the tool assembly 114 is approximated to compress the cut site "C" between the first flange 14 on the anvil 118a and the second flange 16 on the staple cartridge 116a. When the cut site "C" of the anastomosis "A" is properly positioned within the pocket 20 of the wound protector 10 and the anvil 118a and the staple cartridge 116a are approximated, the circular stapling device 100 can be fired by actuating the firing trigger 124 (FIG. 3) to fire staples "S" (FIG. 4A) from the staple cartridge 116a through the first and second flanges 14 and 16 and through the cut site "C" of the anastomosis "A". After the circular stapling device 100 is fired and the wound protector 10 is secured about the cut site "C" of the anastomosis "A", the circular stapling device 100 can be removed from the body lumen "B". As shown in FIGS. 7 and 8, when the wound protector 10 is attached to the anastomosis "A", the cut site "C" is shielded on three sides by the flanges 14, 16 and the annular body 12 of the wound protector 10. In this position, the cut site "C" is protected from waste materials passing through the body lumen "B".

The wound protector 10 can be formed in whole or in part from a plurality of biocompatible and/or bioabsorbable materials including a resilient bioabsorbable and/or biocompatible polymeric material. Examples of suitable bioabsorbable and/or biocompatible polymers include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The wound protector 10 may also be made of a polymer material or materials in combination with radiolucent metal alloys. Alternately, other materials may be used to form the wound protector 10 including biocompatible metals, plastics and composites.

Figure 9:
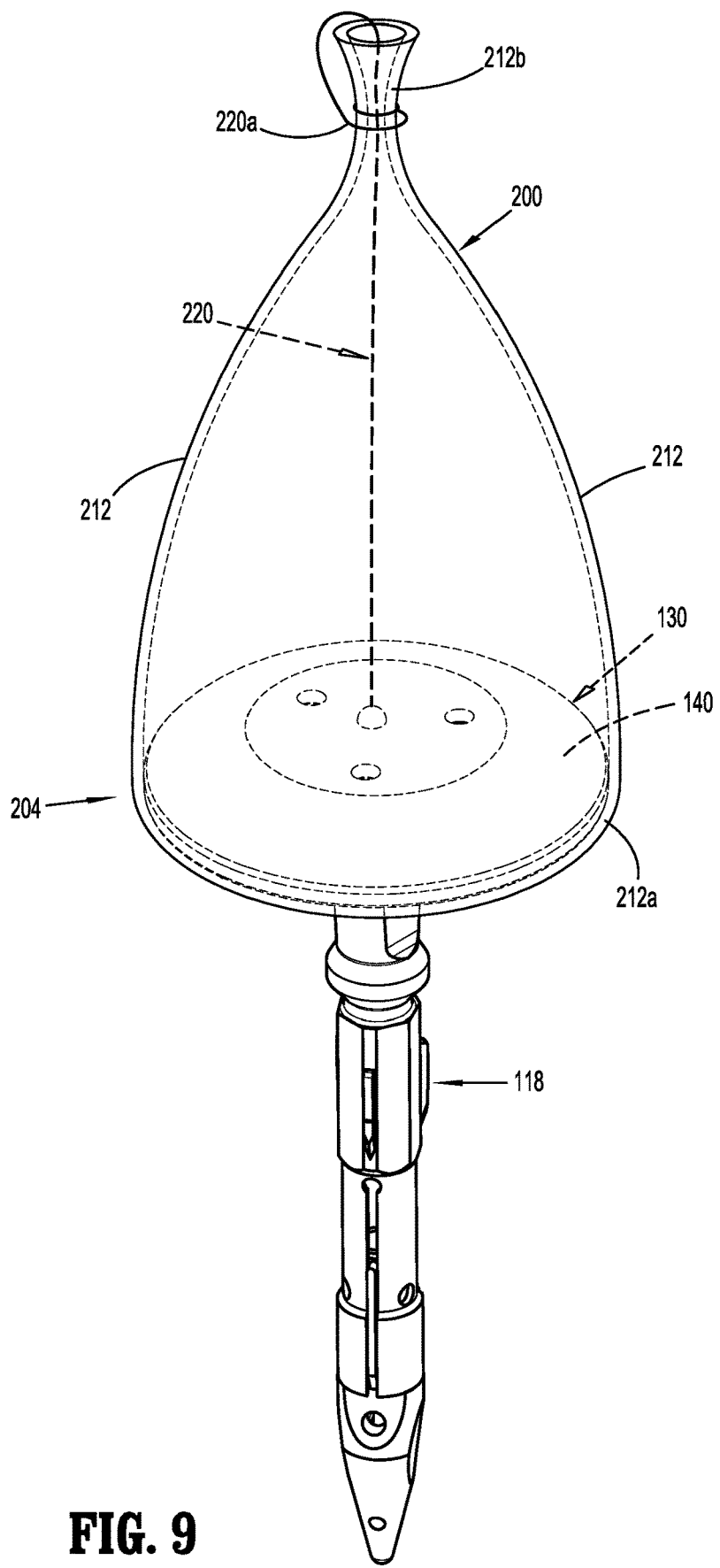
FIG. 9 is another exemplary embodiment of the presently disclosed wound protector supported on an anvil assembly of a circular stapling device.
Figure 10:
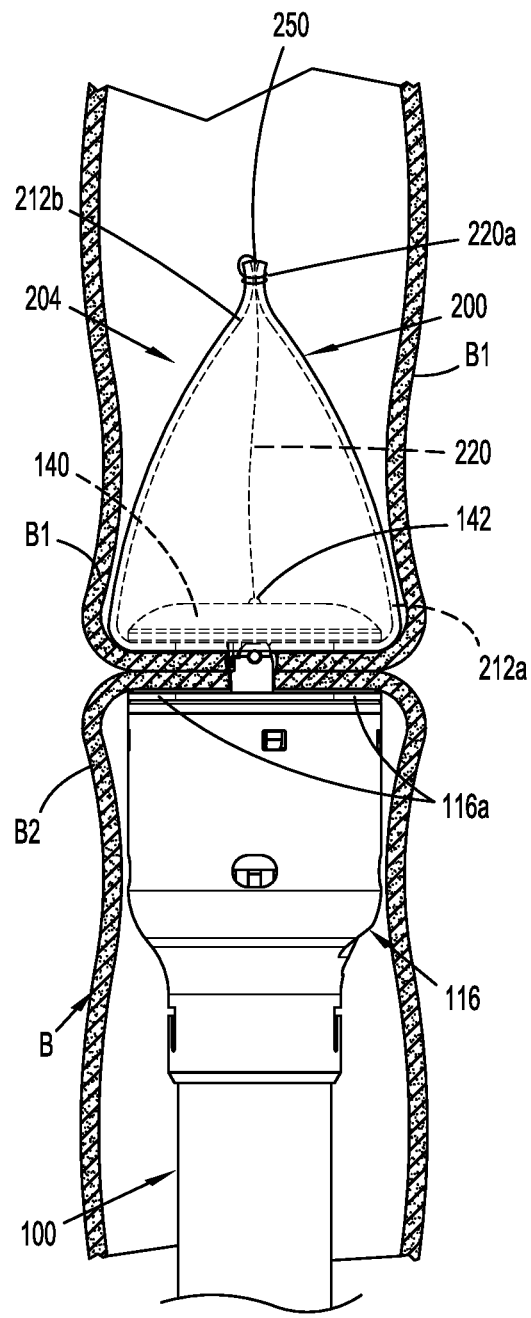
FIG. 10 is a side partial cross-sectional view of the wound protector and anvil assembly shown in FIG. 9 secured to a circular stapling device with the circular stapling device positioned within a body vessel about tissue sections requiring anastomosis after approximation and but prior to firing of the circular stapling device.
Figure 11:
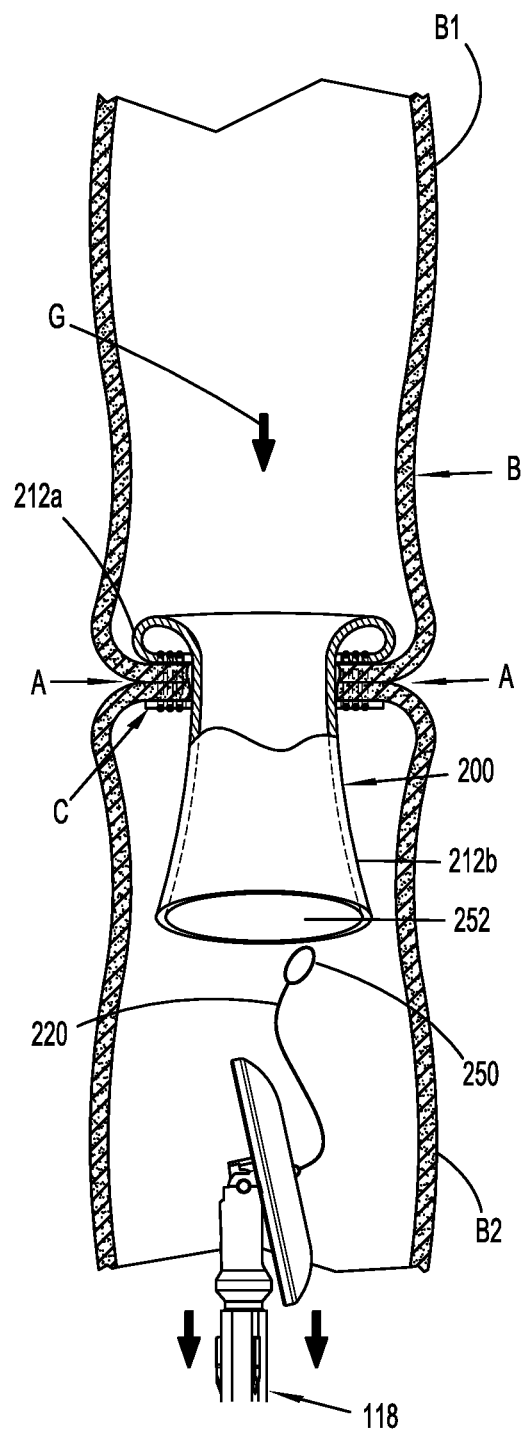
FIG. 11 is a side partial cross-sectional view of the wound protector shown in FIG. 10 positioned within the body vessel about the tissue sections after the circular stapling device has been fired to form the anastomosis and after the wound protector has been inverted through the anastomosis as the circular stapling device is being remove from the body vessel.

FIGS. 9-11 illustrate an alternate embodiment of the presently disclosed wound protector shown generally as wound protector 200. The wound protector 200 is secured to the anvil assembly 118 as described below to form an anvil and wound protector assembly 204. The wound protector 200 includes a tubular body 212 having a first open end 212a and a second open end 212b. The first open end 212a is secured to the anvil 118a (FIG. 4A) of the anvil head 130 of the anvil assembly 118. The second open end 212b of the tubular body 212 is positioned distally of the anvil head 130 such that the anvil head 130 is positioned between the first and second open ends 212a, 212b, respectively, of the tubular body 212 of the wound protector 200. The second end 212b of the tubular body 212b is closed by a tether or suture 220. The tether 220 has a first end 220a that includes a loop 250 that is positioned about the second end 212b of the wound protector 200 to close the second end 212b of the wound protector 200 and a second end 220b that is positioned within the tubular body 212 and is attached to the distal end of the anvil head 130.

In embodiments, the first open end 212a of the wound protector 200 can be secured to the anvil 118a (FIG. 4A) of the anvil head 130 of the anvil assembly 118 using any suitable fastening technique such as adhesion or the like. Similarly, the second end 220b of the tether 220 can be secured to the distal face 140 of the anvil head 130 of the anvil assembly 118 at a securement site 142 (FIG. 10) using any suitable technique. For example, the second end of the suture 220 can be tied to the anvil head 130 through an opening in the anvil head 130 or attached to the anvil head 130 using an adhesive or the like.

Referring to FIGS. 10 and 11, the wound protector 200 can be secured to the body lumen "B" during an anastomosis procedure to join first and second lumen sections "B1" and "B2" of a body lumen "B". More specifically, the anvil assembly 118 supporting the wound protector 200 can be coupled to the circular stapling device 100 and positioned within the body lumen "B". As known in the surgical arts, ends of the first and second body lumens "B1" and "B2" are positioned about the center rod 132 of the anvil assembly 118 between the anvil 118a of the anvil assembly 118 and the staple cartridge 116a of the shell assembly 116 using a purse string suture (not shown) or the like. Once the ends of the body lumens "B1" and "B2" are positioned between the anvil 118a and the staple cartridge 116a, the circular stapling device 100 (FIG. 10) can be approximated to clamp the ends of the body lumens "B1" and "B2" between the staple cartridge 116a and the first end of the 212a of the wound protector 200 which is secured to the anvil 118a (FIG. 4A). When the circular stapling device 100 is fired from this position, the first end 212a of the tubular body 212 of the wound protector 200 is secured to the first and second ends of the body lumen sections "B1" and "B2" and the ends of the body lumens "B1" and "B2" are stapled to each other to form the anastomosis "A". As is known in the art, the knife blade 136 (FIG. 4A) of the circular stapling device 100 passes through the staple cartridge 116a to cut tissue and define an open passage through the body lumen "B" between the body lumen sections "B1" and "B2".

After the circular stapling device 100 is fired to form the anastomosis "A", the circular stapling device 100 can be withdrawn from the body lumen "B" by withdrawing the anvil head 130 through the anastomosis "A" in the direction indicated by arrows "G" in FIG. 11. As the circular stapling device 100 is withdrawn in the direction indicated by arrows "G", the tether 220 on the distal face 140 of the anvil head 130 pulls and inverts the wound protector 200 through the anastomosis "A" to cover and protect the cut site "C" of the anastomosis "A". As the tether 220 pulls and inverts the wound protector 200 through the anastomosis "A", the first end 220a of the tether 220 which defines the loop 250 is pulled off of the second end 212b of the tubular body 212 of the wound protector 200 to allow the second end of the wound protector 200 to open. The tubular body 212 of the wound protector 200 defines a channel 252 (FIG. 11) through the anastomosis "A" to protect the cut site "C" of the anastomosis "A" from waste material passing through the body lumen "B". As shown, the first open end 212a of the tubular body is secured to the upstream side of the anastomosis "A" such that the tubular body 212 of the wound protector 200 is inverted through the anastomosis "A" from the upstream side towards the a downstream side of the anastomosis "A". In this manner, the tubular body 212 of the wound protector 200 covers the anastomosis "A" and is positioned to reduce the likelihood that waste material will collect around the tubular body 212 within the body lumen "B" and potentially uninvert and push the tubular body 212 back through the anastomosis "A".

Figure 13:
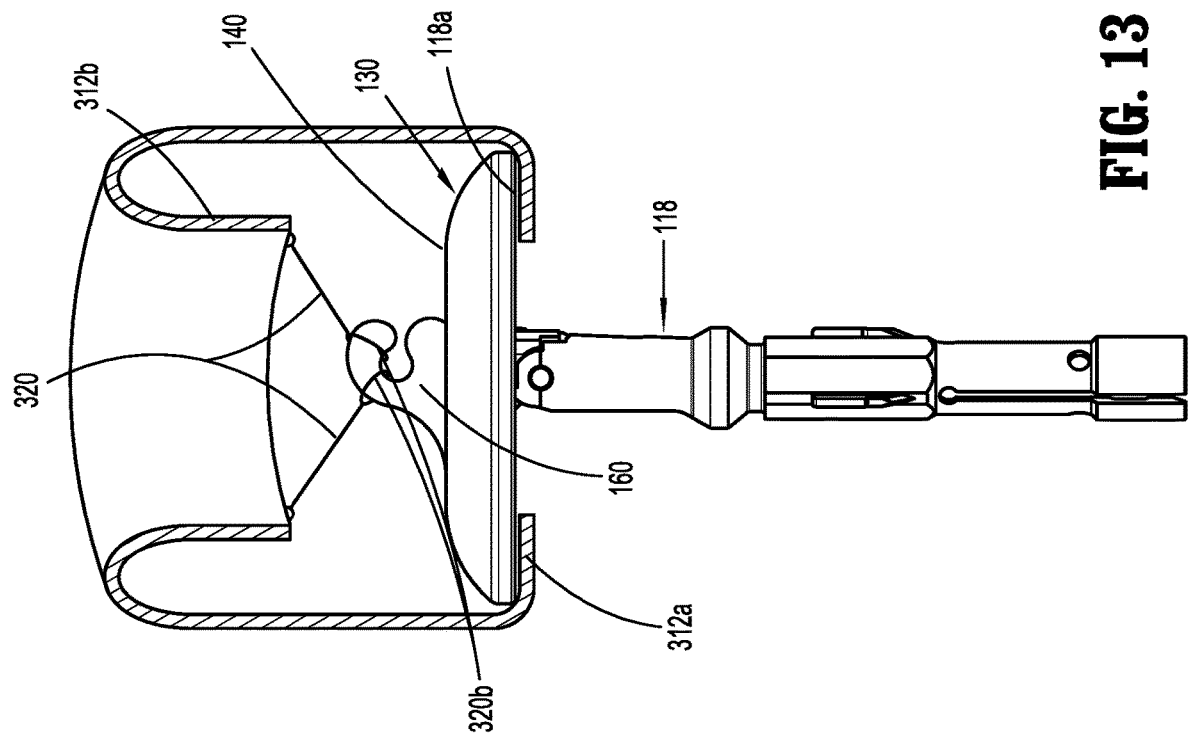
FIG. 13 is a side cross-sectional view of the wound protector shown in FIG. 12 supported on an anvil assembly of a circular stapling device.
Figure 12:
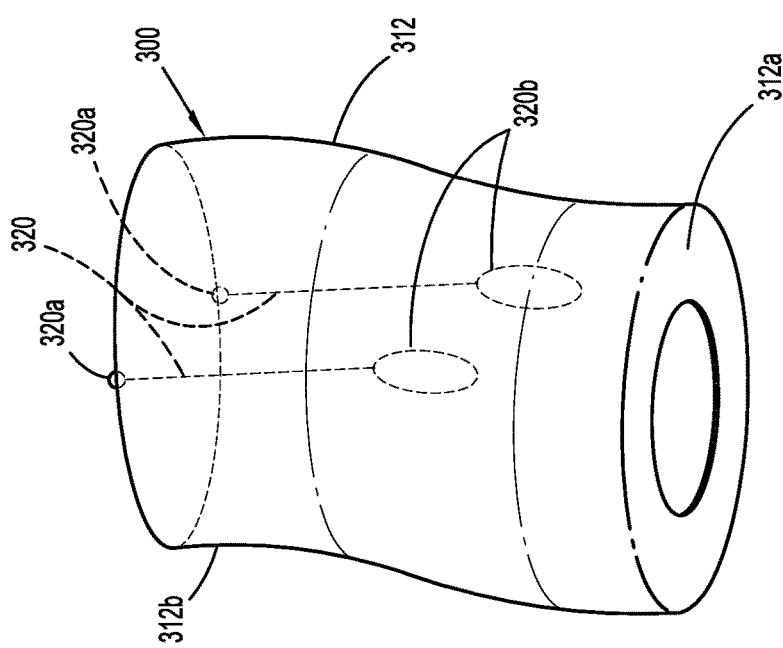
FIG. 12 is a side perspective view of yet another exemplary embodiment of the presently disclosed anastomotic wound protector.
Figure 14:
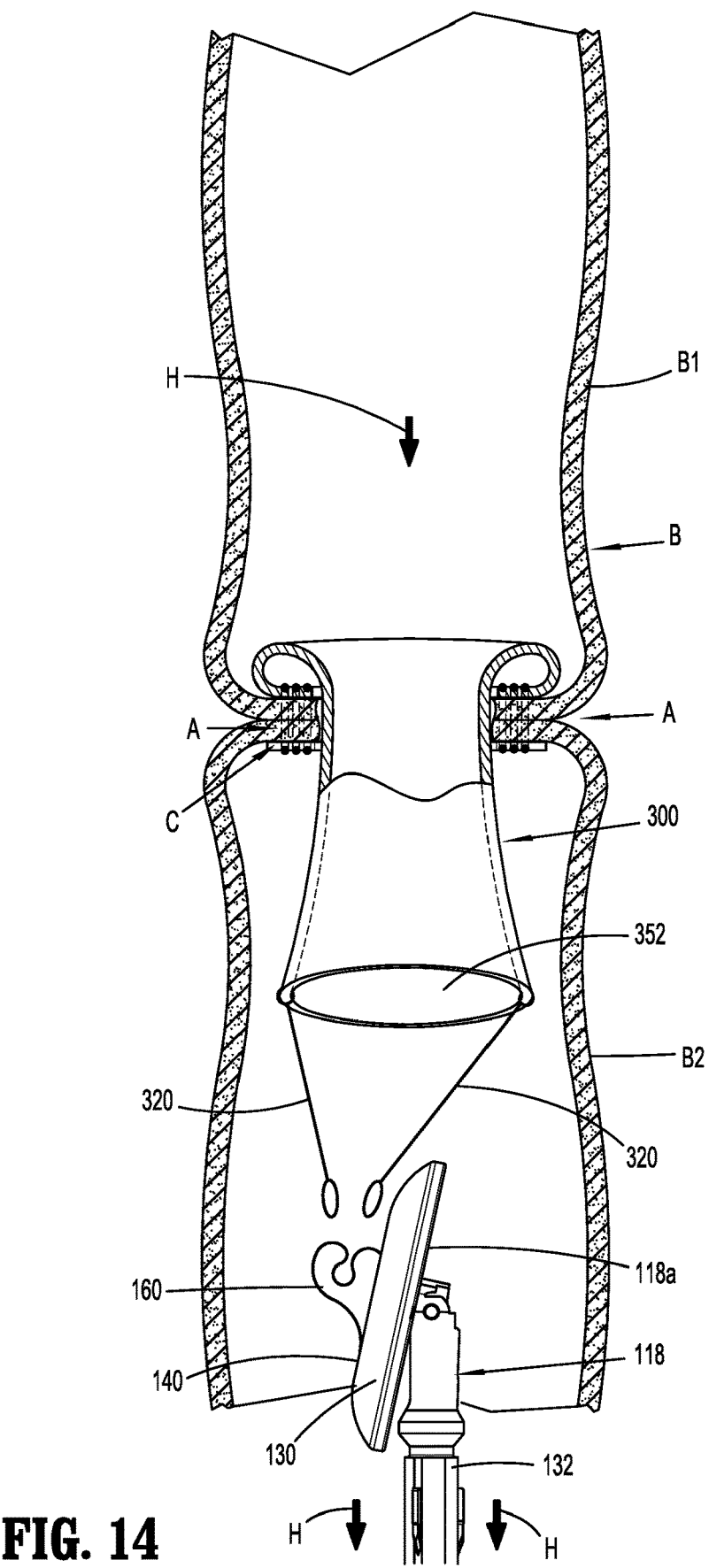
FIG. 14 is a side partial cross-sectional view of the wound protector shown in FIG. 12 positioned within a body vessel about tissue sections after the circular stapling device has been fired to form the anastomosis and after the wound protector has been inverted through the anastomosis as the circular stapling device is being remove from the body vessel.

FIGS. 12-14 illustrate another exemplary embodiment of the presently disclosed wound protector shown generally as 300. The wound protector 300 is similar to the wound protector 200 and includes a tubular body 312 having a first open end 312a and a second open end 312b. The first open end 312a of the tubular body 312 is secured to the anvil 118a of the anvil head 130 of the anvil assembly 118. The second open end 312b of the tubular body 312 is positioned distally of the anvil head 130 such that the anvil head 130 is positioned within the wound protector 300 between the first and second ends 312a, 312b of the tubular body 312. The second end 312b of the tubular body 312 is connected to the distal face 140 of the anvil head 130 by tethers 320. In embodiments, the tethers 320 have first ends 320a that are secured at spaced positions to the second end 312b of the wound protector 300. The tethers 320 extend from the second end 312b of the wound protector 300 and include second ends 320b that define loops 350 that are attached to the distal face 140 of the anvil head 130. In embodiments, the distal face 140 of the anvil head 130 supports a hook 160 that receive the loops 350 on the tethers 320 to secure the second end 312b of the tubular body 212 to the anvil head 130. Alternately, other attachment techniques can be used to secure the tethers 320 to the anvil head 130.

In embodiments, the first open end 312a of the wound protector 300 can be secured to the anvil 118a of the anvil head 130 of the anvil assembly 118 using any suitable fastening technique such as adhesion or the like.

The wound protector 300 can be secured to an anastomosis "A" during an anastomosis procedure in a similar manner to that of wound protector 200. More specifically, referring to FIGS. 13 and 14, the anvil assembly 118 supporting the wound protector 300 can be coupled to the circular stapling device 100 and positioned within the body lumen "B". As known in the surgical arts, the ends of the first and second body lumens "B1" and "B2" are positioned about the center rod 132 of the anvil assembly 118 between the anvil 118a of the anvil assembly 118 and the staple cartridge 116a (FIG. 4A) of the shell assembly 116 using a purse string suture (not shown) or the like. Once the ends of the body lumens "B1" and "B2" are positioned between the anvil 118a and the staple cartridge 116a (FIG. 4A), the circular stapling device 100 (FIG. 1) can be approximated to clamp the ends of the body lumens "B1" and "B2" between the staple cartridge 116a and the first end of the 312a of the wound protector 300 which is secured to the anvil 118a. When the circular stapling device 100 is fired in this position, the first end of the 312a of the wound protector 300 is secured to the first and second ends of the body lumens "B1" and "B2". As can be seen, upon firing, the ends of the body lumens "B1" and "B2" are stapled to each other and to the first end of the wound protector 300 to form the anastomosis "A". As is known in the art, the knife blade 136

(FIG. 4A) of the circular stapling device 100 passes through the staple cartridge 116a to cut tissue and define an open passage through the body lumen "B" between the body lumen sections "B1" and "B2".

After the circular stapling device 100 is fired to form the anastomosis "A", the circular stapling device 100 can be withdrawn from the body lumen "B" by withdrawing the anvil head 130 through the anastomosis "A" in the direction indicated by arrows "H" in FIG. 14. As the circular stapling device 100 is withdrawn in the direction indicated by arrows "H", the tethers 320 secured to the distal face 140 of the anvil head 130 pull and invert the wound protector 300 through the anastomosis "A" to cover and protect the cut site "C" of the anastomosis "A". As the tethers 320 pull and invert the wound protector 300 through the anastomosis "A", the loops 350 on the first ends 320a of the tethers 320 are pulled off of the hook 160 on the distal face 140 of the anvil head 130 to allow anvil head 130 to separate from the wound protector 300 so that the circular stapling device 100 (FIG. 3) can be removed from the body lumen "B". The tubular body 312 of the wound protector 300 defines a channel 352 (FIG. 11) through the anastomosis "A" to protect the cut site "C" of the anastomosis "A".

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil and wound protector assembly comprising:
an anvil assembly including a center rod and an anvil head, the center rod having a distal portion and a proximal portion, the anvil head being supported on the distal portion of the center rod and including a distal face and a proximally facing anvil surface, the anvil surface defining a circular array of staple forming pockets; and
a wound protector having a tubular body, the tubular body having a first end portion secured to the proximally facing anvil surface and a second end portion positioned distally of the distal face of the anvil head such that the anvil head is supported within the tubular body of the wound protector; and
at least one tether having a first end secured to the second end portion of the tubular body of the wound protector at a position distal of the distal face of the anvil assembly and a second end attached to the distal face of the anvil head, the first end of the at least one tether forming a loop that secures the second end portion of the tubular body closed.

2. The anvil and wound protector assembly of claim 1, wherein the first end portion of the tubular body of the wound protector is secured to the proximally facing surface with using an adhesive.

3. The anvil and wound protector assembly of claim 1, wherein the second end of the at least one tether is secured to the distal face of the anvil head using an adhesive.

4. The anvil and wound protector assembly of claim 1, wherein the second end of the at least one tether is tied to the distal face of the anvil head.

5. The anvil and wound protector assembly of claim 1, wherein the anvil head includes a hook and the second end of the at least one tether includes a loop that is secured to the hook.

6. The anvil and wound protector assembly of claim 1, wherein the at least one tether includes two tethers.

7. The anvil and wound protector assembly of claim 5, wherein the loop intersects the second end portion of the tubular body of the wound protector.

8. An anvil and wound protector assembly comprising:
an anvil assembly including a center rod and an anvil head, the center rod having a distal portion and a proximal portion, the anvil head being supported on the distal portion of the center rod and including a distal face and a proximally facing anvil surface, the anvil surface defining a circular array of staple forming pockets; and
a wound protector having a tubular body, the tubular body having a first end portion and a second end portion, the first end portion defining an opening and being secured to the proximally facing anvil surface, and the second end portion positioned distally of the distal face of the anvil head such that the anvil head is supported within the tubular body of the wound protector; and
a tether having a first end portion and a second end portion, the first end portion of the tether disposed about the second end portion of the tubular body of the wound protector at a position distal of the distal face of the anvil assembly, the second end portion of the tether attached to the distal face of the anvil head, wherein the first end portion of the tether forms a loop that closes the opening of the second end portion of the tubular body of the wound protector.

9. The anvil and wound protector assembly of claim 8, wherein the first end portion of the tubular body of the wound protector is secured to the proximally facing surface of the anvil head with an adhesive.

10. The anvil and wound protector assembly of claim 8, wherein the second end portion of the tether is secured to the distal face of the anvil head using an adhesive.

11. The anvil and wound protector assembly of claim 8, wherein the second end portion of the tether is tied to the distal face of the anvil head.

12. The anvil and wound protector assembly of claim 11, wherein the anvil head includes a hook and the second end portion of the tether includes a loop that is secured to the hook.

13. The anvil and wound protector assembly of claim 8, wherein the loop intersects the second end portion of the tubular body of the wound protector.

14. The anvil and wound protector assembly of claim 8, wherein the tether includes first and second tethers.

15. The anvil and wound protector assembly of claim 14, wherein the first end portions of the first and second tethers secured to the second end portion of the wound protector at spaced locations.

16. The anvil and wound protector assembly of claim 15, wherein the second end portions of the first and second tethers are secured to the distal face of the anvil head.

17. The anvil and wound protector assembly of claim 8, wherein the anvil and wound protector assembly are adapted to be coupled to a circular stapling device.

* * * * *